US00PP12223P2

(12) United States Plant Patent
Glicenstein

(10) Patent No.: US PP12,223 P2
(45) Date of Patent: Nov. 27, 2001

(54) CHRYSANTHEMUM PLANT NAMED 'YOMELISSA'

(75) Inventor: Leon Glicenstein, Lebanon, IN (US)

(73) Assignee: Yoder Brothers, Inc., Barberton, OH (US)

( * ) Notice: Subject to any disclaimer, the term of this patent is extended or adjusted under 35 U.S.C. 154(b) by 0 days.

(21) Appl. No.: 09/478,443

(22) Filed: Jan. 6, 2000

(51) Int. Cl.[7] ..... A01H 5/00
(52) U.S. Cl. ..... Plt./287
(58) Field of Search ..... Plt./287, 291, 292

(56) References Cited

U.S. PATENT DOCUMENTS

P.P. 8,572 * 2/1994 Wain ..... Plt./287
P.P. 8,782 * 6/1994 Fuess ..... Plt./287
P.P. 8,898 * 9/1994 Glicenstein ..... Plt./287
P.P. 8,979 * 11/1994 Glicenstein ..... Plt./287
P.P. 10,901 * 5/1999 VandenBerg ..... Plt./287

* cited by examiner

*Primary Examiner*—Howard J. Locker
(74) *Attorney, Agent, or Firm*—C. A. Whealy

(57) ABSTRACT

A distinct cultivar of Chrysanthemum plant named 'Yomelissa', characterized by its uniformly mounded plant habit; freely branching growth habit; uniform flowering; decorative-type inflorescences that are about 5.6 cm in diameter; attractive dark lavender ray florets; numerous inflorescences per plant; and excellent garden performance.

1 Drawing Sheet

BACKGROUND OF THE INVENTION

The present invention relates to a new and distinct cultivar of Chrysanthemum plant, botanically known as *Dendranthema grandiflora* and hereinafter referred to by the cultivar name Yomelissa.

The new cultivar is a product of a planned breeding program conducted by the Inventor in Salinas, Calif. and Alva, Fla. The objective of the breeding program is to create new garden-type Chrysanthemum cultivars having inflorescences with desirable inflorescence forms, attractive floret colors and good garden performance.

The new cultivar originated from a cross made by the Inventor in Salinas, Calif., in December, 1995, of the *Dendranthema grandiflora* cultivar Debonair, disclosed in U.S. Plant Pat. No. 5,324, as the female, or seed, parent with an unidentified proprietary seedling selection as the male, or pollen, parent.

The cultivar Yomelissa was discovered and selected by the Inventor as a flowering plant within the progeny of the stated cross in a controlled environment in Alva, Fla. in November, 1996. The selection of this plant was based on its desirable inflorescence form, attractive ray floret color and excellent garden performance.

Asexual reproduction of the new cultivar by terminal cuttings taken in a controlled environment in Alva, Fla. has shown that the unique features of this new Chrysanthemum are stable and reproduced true to type in successive generations.

SUMMARY OF THE INVENTION

The cultivar Yomelissa has not been observed under all possible environmental conditions. The phenotype may vary somewhat with variations in environment such as temperature, daylength and light intensity, without, however, any variance in genotype.

The following traits have been repeatedly observed and are determined to be the unique characteristics of 'Yomelissa'. These characteristics in combination distinguish 'Yomelissa' as a new and distinct cultivar:

1. Uniformly mounded plant habit.

2. Freely branching, dense, full plants.

3. Uniform flowering.

4. Decorative-type inflorescences that are about 5.6 cm in diameter.

5. Attractive dark lavender ray florets.

6. Numerous inflorescences per plant.

7. Excellent garden performance.

The new Chrysanthemum is similar to the parent cultivar, Debonair. However in side-by-side comparisons under commercial practice, plants of the new Chrysanthemum differ from plants of the cultivar Debonair in the following characteristics:

1. Plants of the new Chrysanthemum are more compact and more uniformly mounded than plants of the cultivar Debonair.

2. Plants of the new Chrysanthemum flower about 10 days later than plants of the cultivar Debonair under natural season photoperiodic conditions.

3. Plants of the new Chrysanthemum have larger inflorescences and are more freely and uniformly flowering than plants of the cultivar Debonair.

4. Ray florets of plants of the new Chrysanthemum are broader and slightly darker in color than ray florets of the cultivar Debonair.

BRIEF DESCRIPTION OF THE PHOTOGRAPHS

The accompanying photographs illustrate the overall appearance of the new Chrysanthemum. These photographs show the colors as true as it is reasonably possible to obtain in colored reproductions of this type. Colors in the photographs may differ slightly from the color values cited in the detailed botanical description which more accurately describe the actual colors of the new Chrysanthemum.

The photograph at the top of the sheet comprises a top perspective view of a typical flowering plant of 'Yomelissa'.

The photograph at the bottom of the sheet comprises a close-up view of typical inflorescences of the cultivar 'Yomelissa'.

DETAILED BOTANICAL DESCRIPTION

In the following description, color references are made to The Royal Horticultural Society Colour Chart except where general terms of ordinary dictionary significance are used. The following observations and measurements describe plants grown in Pendleton, S.C., under conditions which approximate thoses generally used in commercial garden Chrysanthemum production. One rooted cutting was planted in a 15-cm container on Jul. 26, 1999 and plants were grown under natural season conditions. Plants were not pinched, that is, the terminal apex was not removed to enhance branching. Measurements and numerical values represent average for typical flowering plants.

Botanical classification: *Dendranthema grandiflora* cultivar Yomelissa.

Commercial classification: Decorative-type garden chrysnthemum.

Parentage:

*Female parent.*—*Dendranthema grandiflora* cultivar Debonair, disclosed in U.S. Plant Pat. No. 5,324.

*Male parent.*—Unidentified proprietary seedling selection.

Progation:

*Type.*—Terminal tip cuttings.

*Time to rooting.*—Seven to ten days with soil temperatures of 21° C.

*Rooting habit.*—Fine, fibrous and well-branched.

Plant description:

*Appearance.*—Perennial herbaceous decorative-type garden Chrysanthemum. Inverted triangle; mounded plant form. Stems initally upright, then outwardly spreading giving a uniformly mounded appearance to the plant. Freely branching with lateral branches potentially developing at every node.

*Plant height.*—About 22.5 cm.

*Plant spread.*—About 39 cm.

*Stems.*—Texture: Pubescent. Color: Between 146A and 144A.

*Foliage description.*—Leaf arrangement: Alternate. Length: About 4.8 cm. Width: About 4.1 cm. Apex: Cuspidate. Base: Mostly truncate. Margin: Palmately lobed, sinuses divergent. Texture: Upper surface sparsely pubescent; lower surface moderately pubescent. Veins prominent on lower surface. Petiole length: About 1.1 cm. Petiole diameter: About 3 mm. Color: Young foliage upper surface: 147A. Young foliage lower surface: 147B. Mature foliage upper surface: 147A. Mature foliage lower surface: 147B. Venation upper surface: 147A to 147B. Venation lower surface: 147B.

Inflorescence description:

*Appearance.*—Decorative-type inflorescence form with spatulate to elongated oblong-shaped ray florets. Inflorescences borne on terminals above foliage, arising from leaf axils. Disk and ray florets arranged acropetally on a capitulum. About 125 inflorescences per plant.

*Flowering response.*—Under natural season conditions, plants flower in the autumn about 75 days after planting.

*Inflorescence bud.*—Height: About 5.5 mm. Diameter: About 7.5 mm. Color: Between 146A and 147A.

*Inflorescence size.*—Diameter: About 5.6 cm. Depth (height): About 1.6 cm. Diameter of disc: Less than 3 mm.

*Ray florets.*—Shape: Spatulate to elongated oblong, concave. Length: About 2.6 cm. Width: About 1.1 cm. Apex: Minutely dentate. Margin: Entire. Texture: Smooth, glabrous, satiny; iridescent. Orientation: Initially upright, then perpendicular to the peduncle. Number of ray florets per inflorescence: About 257. Color: When opening, upper surface: Apex, 77A; base, white. When opening, lower surface: Apex, 77A; base, white. Opened inflorescence, upper surface: 77B to 75A; base, 75B. Opened inflorescence, lower surface: 75D.

*Disc florets.*—Shape: Tubular, apex dentate. Length: About 4 mm. Width: Apex: About 1.5 mm. Base: About 1 mm. Number of disc florets per inflorescence: Less than ten. Color: Immature: 154A. Mature: Apex: 14A. Mid-section: Greenish white. Base: White.

*Peduncle.*—Aspect: Flexible, angled about 45 to 50° to the stem. Length: First peduncle: About 4.3 cm. Third peduncle: About 6.5 cm. Diameter: About 2.5 mm. Texture: Pubescent. Color: Between 144A and 146A.

*Reproductive organs.*—Androecium: Present on disc florets only. Anther color: 14A. Pollen: Scarce. Pollen color: 14A. Gynoceium: Present on both ray and disc florets.

*Seed.*—Seed production has not been observed.

Disease resistance: Plants of the new Chrysanthemum have not been shown to be resistant to pathogens common to Chrysanthemums.

It is claimed:

1. A new and distinct cultivar of Chrysanthemum plant named 'Yomelissa', as illustrated and described.

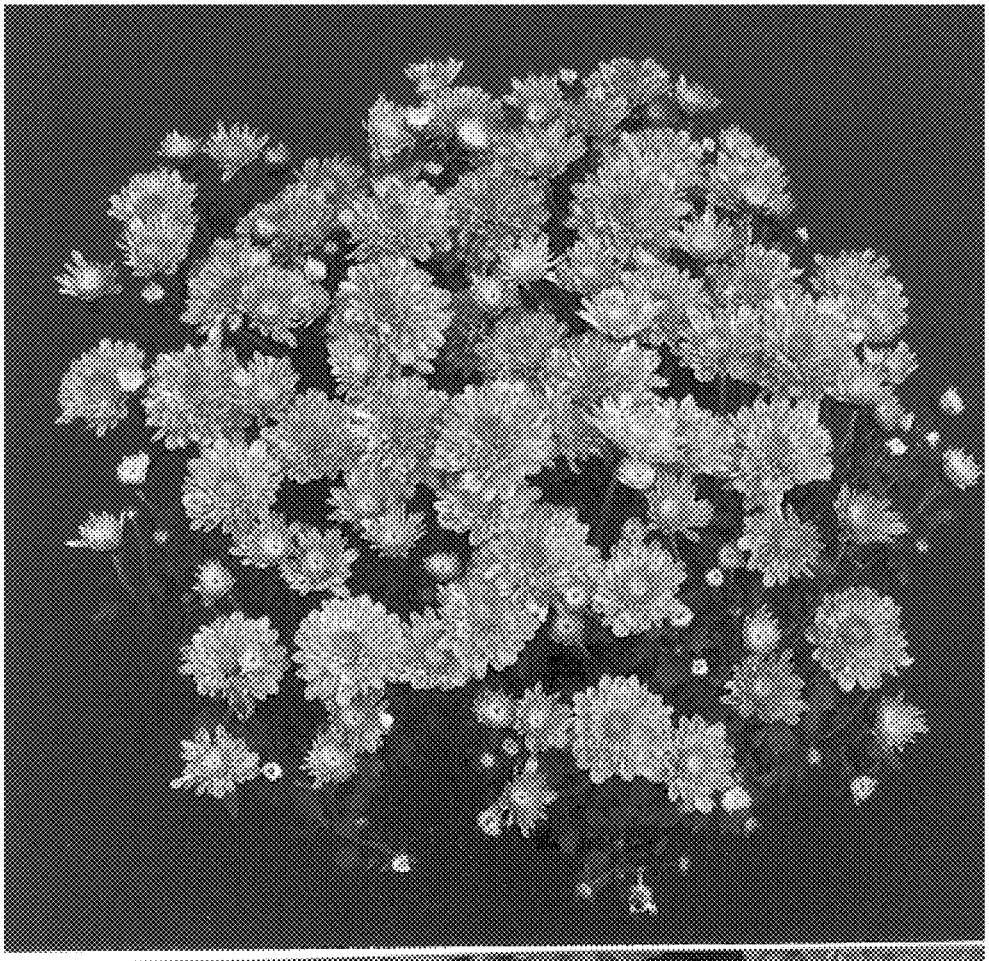
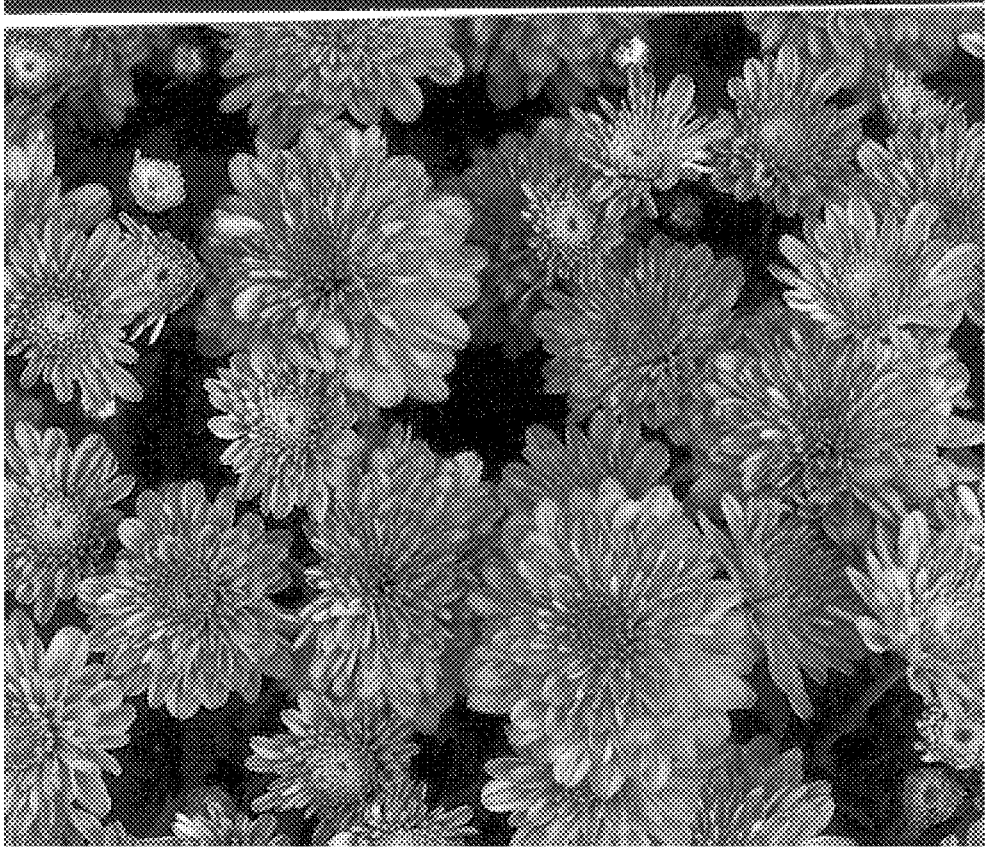

* * * * *